US012589108B2

(12) United States Patent
Zhao et al.

(10) Patent No.: US 12,589,108 B2
(45) Date of Patent: Mar. 31, 2026

(54) INJECTABLE BIFUNCTIONAL HYDROGEL WITH ANTIBACTERIAL ACTIVITY AS WELL AS THE PREPARATIVE METHOD AND THE USE THEREOF

(71) Applicant: SICHUAN UNIVERSITY, Chengdu (CN)

(72) Inventors: Hang Zhao, Chengdu (CN); Jiang Liu, Chengdu (CN); Yanan Zhang, Chengdu (CN); Xianglong Han, Chengdu (CN); Qianming Chen, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 737 days.

(21) Appl. No.: 17/436,227

(22) PCT Filed: May 29, 2020

(86) PCT No.: PCT/CN2020/093461
§ 371 (c)(1),
(2) Date: Sep. 3, 2021

(87) PCT Pub. No.: WO2021/169075
PCT Pub. Date: Sep. 2, 2021

(65) Prior Publication Data

US 2022/0152076 A1 May 19, 2022

(30) Foreign Application Priority Data

Feb. 27, 2020 (CN) ......................... 202010126522.1

(51) Int. Cl.

| | |
|---|---|
| ***A61K 31/7076*** | (2006.01) |
| ***A61K 9/00*** | (2006.01) |
| ***A61K 9/06*** | (2006.01) |
| ***A61P 31/04*** | (2006.01) |

(52) U.S. Cl.
CPC ........ *A61K 31/7076* (2013.01); *A61K 9/0019* (2013.01); *A61K 9/06* (2013.01); *A61P 31/04* (2018.01)

(58) Field of Classification Search
CPC ... A61K 31/7076; A61K 9/0019; A61K 31/04
USPC .......................................................... 514/45
See application file for complete search history.

(56) References Cited

U.S. PATENT DOCUMENTS 5,420,115 A * 5/1995 Tisdale .............. A61K 31/7076
536/27.61

FOREIGN PATENT DOCUMENTS

CN 106397795 A 2/2017
CN 108498543 A 9/2018

* cited by examiner

*Primary Examiner* — Ganapathy Krishnan
(74) *Attorney, Agent, or Firm* — NKL Law; Allen Xue

(57) ABSTRACT

An injectable bifunctional hydrogel has antibacterial activity. The bifunctional hydrogel is a hydrogel prepared by dissolving nucleoside analogues in a solvent. The nucleoside analog has a structure of formula I. It can be a candidate drug for the local injection treatment of periodontal disease, and it also has potential application prospects in the minimally invasive treatment of craniofacial bone tissue defects.

(I)

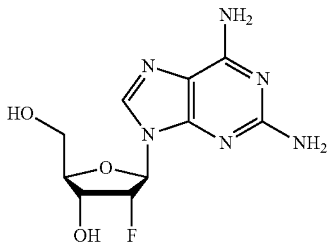

8 Claims, 7 Drawing Sheets

INJECTABLE BIFUNCTIONAL HYDROGEL WITH ANTIBACTERIAL ACTIVITY AS WELL AS THE PREPARATIVE METHOD AND THE USE THEREOF

TECHNICAL FIELD

The present invention belongs to biomedical materials, and specifically relates to an injectable bifunctional hydrogel with antibacterial activity, as well as the preparative method and the use thereof.

BACKGROUND ART

Periodontal disease is a chronic infectious disease, and studies have shown that its main pathogenic factor is bacteria. Periodontitis is treated by curettage and flatting root surface to remove plaque and tartar. However, due to the complex anatomical structure of the tooth and the deeper periodontal pocket, it is not easy to remove some plaques and tartars, and the auxiliary antibacterial treatment is required. Adjuvant antibacterial treatment is mainly divided into two ways, i.e. oral antibiotics and topical medication. Oral antibiotics for the treatment of periodontitis have the following disadvantages: insufficient antibiotic concentration in the periodontal pocket, rapid decline in plasma antibiotic concentration to sub-therapeutic levels, prone to causing bacterial resistance, frequent medications for patients, and high compliance requirements for patients. In view of above shortcomings, there have been a large number of researches focusing on topical medication for antibacterial therapy, which uses local drug delivery systems for administration. The local drug delivery system directly reaches the periodontal pocket, and this treatment way has the following advantages: direct contact with the diseased site, improving patient compliance, avoiding gastrointestinal reactions caused by oral administration, avoiding first-pass metabolism in the liver, enhancing the therapeutic effect of drugs, reducing the treatment cost, providing a reliable drug delivery route for patients unable to swallow, a safer and more convenient route of administration, prolonging the action time, as well as a non-invasive, painless and simple administration way. Therefore, currently, topical drugs such as minocycline, metronidazole gel, and biodegradable chlorhexidine gluconate tablets are mainly used in clinical. The drugs are directly placed in the periodontal pocket to achieve antibacterial effects, that has become the main auxiliary method for antibacterial treatment.

As a carrier material for local drug delivery, hydrogel has attracted wide attention because of its unique structure and composition similar to natural extracellular matrix. The hydrogel prepared from the polymer can expand its application in local drug-carrying materials. In addition, the local drug delivery system is administrated in the periodontal pocket by injection, which has become the main local drug delivery way due to the advantages of minimal invasion or non-invasion, simple operation, and reduced frequency of medication, etc. Therefore, the drug delivery system of injectable hydrogel has gradually become a research hotspot in recent years. At present, most researches on injectable hydrogels for periodontal treatment are thermosensitive polymer hydrogels, characterized in that they are solutions before injection and become gel when injected into the target location of the body. For example, in the investigations of using chitosan (CS), quaternized chitosan (HTCC) and α,β-glycerophosphate (α,β-GP), injectable thermosensitive hydrogels with antibacterial properties (CS-HTCC/αβ-GP) have successfully been designed and prepared. Although this hydrogel has both antibacterial activity and injectable ability, the sol-gel transition time is 3 minutes (37° C.). After the solution is injected into the target site, it may penetrate into the surrounding tissues or be affected by the surrounding environment, which limits the formation of hydrogel, and may further cause toxicity problems. Among the physically cross-linked hydrogels, although for some of the hydrogels the influence of the surrounding environment on the cross-linking process can be ignored, and they have a fast self-repairing speed and can quickly perform the function of the carrier, but most of the hydrogels do not have antibacterial properties, such as the mixture of Poloxamer 407 (PX) and polyacrylic acid (PAA) is a low-viscosity liquid at room temperature, and has shear-thinning behavior, which makes it have syringeability and gel rapidly at body temperature, but the hydrogel does not have antibacterial properties.

Among the physically cross-linked hydrogels, although some of the hydrogels can ignore the influence of the surrounding environment on the cross-linking process, have a fast self-repairing rate, and quickly exert the function of the carrier, but most of them do not have antibacterial properties. For example, the mixture of Poloxamer 407 (PX) and polyacrylic acid (PAA) is a low-viscosity liquid at room temperature with shear thinning behavior, which confers it a syringeability and makes it rapid gelling at body temperature, however, the hydrogel does not have antibacterial properties. These hydrogel carriers without antibacterial activity need to be added with antibacterial drugs to realize antibacterial effects. However, there may be the following problems: the loaded drugs may affect the gel formation, and thus the drugs are not easy to be loaded, leading to the loss of drug effects. After being injected into the body, the leakage of the loaded drug may lead to toxic and side effects on local cell tissues, and the purpose of the drug-loading system for delayed release cannot be achieved. There are few reports on injectable antibacterial local drug delivery systems, and there is no report that a hydrogel with both antibacterial activity and injectable ability caused by shear thinning may be used for antibacterial treatment of periodontitis by local injection.

Natural nucleosides, a kind of endogenous small molecules, are one of the building blocks of supramolecular hydrogels, and under the action of reversible non-covalent bonds, they self-assembly form hydrogels with a three-dimensional network structure. Based on their good compatibility, they have been extensively studied. Guanosine (G), as one of building blocks for the simplest supramolecular hydrogel, has poor stability and requires a higher concentration of ionic solution, which hinders its further application in the biological field. Lots of related researches are intended to improve the performance of hydrogels. Nucleoside analogs are a class of small molecules that have been widely investigated. Seela et al. have recently discovered that isoguanosine (isoG), an isomer of G, can self-assemble into a more stable hydrogel, but the resultant hydrogel cannot be injected and has no antibacterial properties. When G and isoG are mixed at a ratio of 1:1 and then dissolved in the $K^+$ solution, a supramolecular hydrogel can be formed with good stability, short self-repairing time, and injectability, but it also does not have antibacterial properties. There are also reports that 2'-deoxy-2'-fluoroguanosine forms a poorly stable hydrogel in KCl solution, and can form a stable antibacterial hydrogel in an $Ag^+$ aqueous solution, but the hydrogel doesn't have injectable properties.

Therefore, it is necessary to explore a hydrogel that combines an injectable ability from shear thinning with antibacterial effect, and at the same time has antibacterial activities by local injection, as well as plays a potential effect on local non-invasive treatment of periodontal in the future.

CONTENT OF THE INVENTION

The object of the present invention is to provide an injectable bifunctional hydrogel with antibacterial activity, as well as the preparative method and the use thereof.

The present invention provides an injectable bifunctional hydrogel with antibacterial activity, that is a hydrogel prepared by dissolving nucleoside analogues in a solvent;

The structure of said nucleoside analog is shown by formula I:

Formula I

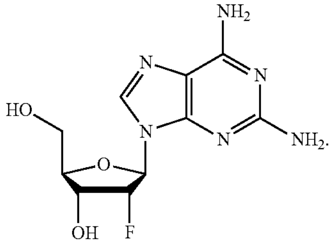

Further, the concentration of the nucleoside analog in the hydrogel is 1.67 w/v %~5 w/v %; Preferably, the concentration of the nucleoside analog in the hydrogel is 2.5 w/v %~5 w/v %.

Further, the solvent is water or phosphate buffer.

Further, the preparative method of said hydrogel includes that the nucleoside analog is dissolved in a solvent with heating, and then cooled to room temperature.

The present invention provides a preparative method of the bifunctional hydrogel mentioned above, that includes the following steps:

The nucleoside analog is dissolved in a solvent with heating, and then cooled to room temperature.

Further, after it is dissolved in a solvent, the concentration of the nucleoside analog is 1.67 w/v %~5 w/v %;

Preferably, the concentration of the nucleoside analog is 2.5 w/v %~5 w/v %.

The present invention further provides the use of the bifunctional hydrogel mentioned above in the preparation of tissue repair materials and/or local injection of drug for treatment of periodontal disease.

Further, the tissue repair material is that used in craniomaxillofacial bone tissue; and/or, the periodontal disease is periodontitis.

The present invention further provides a local injection of drug for treatment of periodontal disease, that is prepared from above bifunctional hydrogel as the active substance, with the addition of pharmaceutically acceptable excipients or auxiliary components;

Preferably, said periodontal disease is periodontitis.

The present invention further provides the use of nucleoside analogue with the structure of formula I in the preparation of antibacterial drugs and/or biomedical materials with antibacterial effects:

Formula I

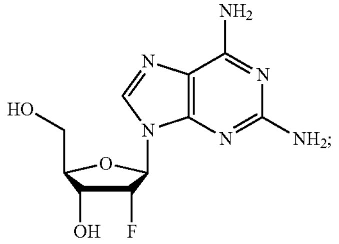

Preferably, the biomedical material is a tissue repair material.

In the present invention, room temperature means 25±5° C.

In the prior art, there are few studies on the nucleoside analogue of 2-amino-2'-fluoro-2'-deoxyadenosine, and the nucleoside analogue has not been found to have antibacterial effect, nor has the analogues been used to prepare a hydrogel with both injectability and antibacterial properties.

This nucleoside analogue is used in the present invention to successfully construct a hydrogel with both injectability and antibacterial properties, which is the first hydrogel reported so far. The hydrogel has ultra-high strength, and its excellent mechanical properties are manifested in its MPa-level storage modulus and anti-compressive strength: 5.0% hydrogel has a storage modulus of up to 1 MPa, which is the highest value of injectable supramolecular hydrogel formed so far by self-assembly of gelling agents with low molecular weight. The hydrogel has good shear-thinning and self-repairing performances, as well as good injectable property. It is in a gel state before injection, and gels immediately after injection. After injection with a syringe at 37° C., its changing from liquid agent to solid gel takes only a few seconds. In most research reports, high intensity and shear-thinning properties are often not available at the same time, but the hydrogel of the present invention is an injectable hydrogel with both of them, that play an important role in the minimally invasive treatment of weight-bearing tissues.

In addition, the hydrogel of the present invention has a potential broad-spectrum antibacterial properties, and it has a good antibacterial effect on model strains of G(+) and G(−) bacteria, and at the same time also has a good antibacterial effect on *Streptococcus mutans* of oral pathogenic bacteria G(+) as well as G(−) *Porphyromonas gingivalis*, that solve the problem currently existed in local non-invasive antibacterial drug system of periodontium, such as the carrier having no or poor antibacterial properties, low efficiency of embedding drugs, easy to leak, releasing too fast, and so on. The hydrogel of the present invention also has good biocompatibility, has good stability at room temperature, is stable when injected into the human body, is degradable in the human body, and is convenient to use. Moreover, the preparative process of the hydrogel according to the present invention is simple, convenient, and environmentally friendly: it can be obtained by dissolving in $dH_2O$ and PBS under heating, followed by cooling.

In summary, a bifunctional hydrogel is prepared in the present invention by a simple and green method. The hydrogel has good shear-thinning and self-repairing performances, good injectability, quick gelling, and is easy to use. The hydrogel also has excellent mechanical properties, as well as extremely high strength, storage modulus and anti-compressive strength up to MPa level. At the same time, the hydrogel has a good antibacterial effect, and has a good inhibitory effect on the growth of model strains and oral pathogens. In addition, the hydrogel has good stability at room temperature, can be stored for a long time, and can be quickly degraded after being implanted in the human body, and has good biocompatibility. With these outstanding features, the hydrogel of the present invention is expected to be a candidate drug for the local injection treatment of periodontal disease, and it also has potential application prospects in the minimally invasive treatment of craniofacial bone tissue defects.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
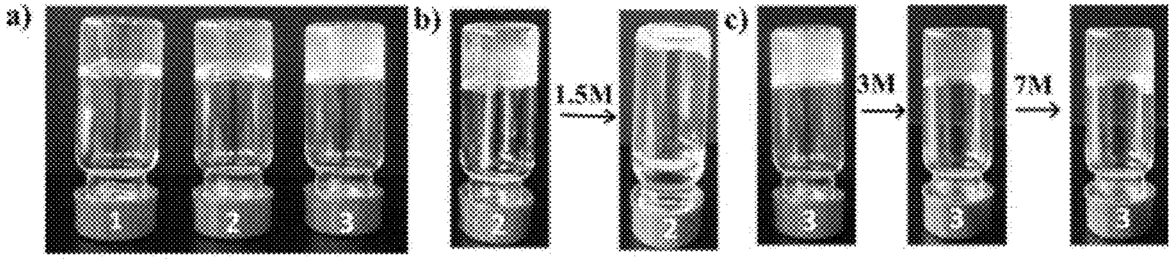
FIG. 1 is an inversion experimental diagram of the bifunctional hydrogel prepared in Examples 1~3 of the present invention: a) An inversion experimental diagram of hydrogels with different concentrations of nucleoside analogs in a small tube, in which 1 represents 1.67% hydrogel prepared in Example 1, 2 represents 2.5% hydrogel prepared in Example 2, and 3 represents 5.0% hydrogel prepared in Example 3; b) The stable time of 2.5% hydrogel at room temperature, in which 1.5M means 1.5 months; c) The stable time of 5.0% hydrogel at room temperature, in which 3M means 3 months, and 7M means 7 months.

The starting materials and equipment used in the examples of the present invention are all known products and can be obtained by purchasing commercially available products.

Among them, the nucleoside analog used in the specific examples is all 2-amino-2'-fluoro-2'-deoxyadenosine, with the molecular formula $C_{10}H_{13}FN_6O_3$, and the molecular weight 284.25, and the structural formula is:

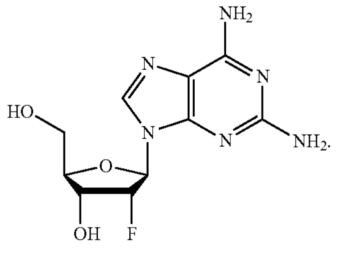

Example 1 the Preparation of Bifunctional Hydrogel of the Present Invention

The bifunctional hydrogel was constructed by "one-step method", and the detailed preparative process was as follows:

1.67 g nucleoside analog was completely dissolved in 100 mL phosphate buffered saline (PBS) under heating, and then cooled to room temperature to obtain the bifunctional hydrogel (1.67% hydrogel) of the present invention. The concentration of nucleoside analog in bifunctional hydrogel was 1.67 w/v %, and the transition temperature of bifunctional hydrogel was 35° C. (transition temperature means the temperature at which hydrogel begins to transform from a gel state to a liquid state).

Example 2 the Preparation of Bifunctional Hydrogel of the Present Invention

The bifunctional hydrogel was constructed by "one-step method", and the detailed preparative process was as follows:

2.5 g nucleoside analog was completely dissolved in 100 mL phosphate buffered saline (PBS) under heating, and then cooled to room temperature to obtain the bifunctional hydrogel (2.5% hydrogel) of the present invention. The concentration of nucleoside analog in bifunctional hydrogel was 2.5 w/v %, and the transition temperature of bifunctional hydrogel was 37° C. (transition temperature means the temperature at which hydrogel begins to transform from a gel state to a liquid state).

Example 3 the Preparation of Bifunctional Hydrogel of the Present Invention

The bifunctional hydrogel was constructed by "one-step method", and the detailed preparative process was as follows:

5.0 g nucleoside analog was completely dissolved in 100 mL phosphate buffered saline (PBS) under heating, and then cooled to room temperature to obtain the bifunctional hydrogel (5.0% hydrogel) of the present invention. The concentration of nucleoside analog in bifunctional hydrogel was 5.0 w/v %, and the transition temperature of bifunctional hydrogel was 47° C. (transition temperature means the temperature at which hydrogel begins to transform from a gel state to a liquid state).

Example 4 the Preparation of Bifunctional Hydrogel of the Present Invention

The bifunctional hydrogel was constructed by "one-step method", and the detailed preparative process was as follows:

1.67 g nucleoside analog was completely dissolved in 100 mL distilled water ($dH_2O$) under heating, and then cooled to room temperature to obtain the bifunctional hydrogel (1.67% hydrogel) of the present invention. The concentration of nucleoside analog in bifunctional hydrogel was 1.67 w/v %, and the transition temperature of bifunctional hydrogel was 35° C. (transition temperature means the temperature at which hydrogel begins to transform from a gel state to a liquid state).

Example 5 the Preparation of Bifunctional Hydrogel of the Present Invention

The bifunctional hydrogel was constructed by "one-step method", and the detailed preparative process was as follows:

2.5 g nucleoside analog was completely dissolved in 100 mL distilled water ($dH_2O$) under heating, and then cooled to room temperature to obtain the bifunctional hydrogel (2.5% hydrogel) of the present invention. The concentration of nucleoside analog in bifunctional hydrogel was 2.5 w/v %, and the transition temperature of bifunctional hydrogel was 37° C. (transition temperature means the temperature at which hydrogel begins to transform from a gel state to a liquid state).

Example 6 the Preparation of Bifunctional Hydrogel of the Present Invention

The bifunctional hydrogel was constructed by "one-step method", and the detailed preparative process was as follows:

5.0 g nucleoside analog was completely dissolved in 100 mL distilled water ($dH_2O$) under heating, and then cooled to room temperature to obtain the bifunctional hydrogel (5.0% hydrogel) of the present invention. The concentration of nucleoside analog in bifunctional hydrogel was 5.0 w/v %, and the transition temperature of bifunctional hydrogel was 47° C. (transition temperature means the temperature at which hydrogel begins to transform from a gel state to a liquid state).

The beneficial effects of the present invention were demonstrated by following specific experimental examples.

Experimental Example 1. The Properties of Bifunctional Hydrogel of the Present Invention 1. Experimental Method Whether the hydrogels prepared in examples 1~6 were successfully constructed was detected by a small tube inversion experiment. The gelation properties of the hydrogels prepared in Examples 2~6 were detected by conventional methods.

2. Experimental Results

The small tube inversion experiment confirmed that the hydrogels prepared in Examples 1~6 of the present invention were all successfully constructed. FIG. 1 shows inverted diagrams of the hydrogels prepared in Examples 1~3. From a) in FIG. 1, it could be shown that as the concentration of the nucleoside analog increased, the appearance of the hydrogel changed from transparent to translucent. In FIG. 1, b) and c) are the stable times of 2.5% hydrogel and 5.0% hydrogel at room temperature, respectively, and as shown, the stable time of 2.5% hydrogel at room temperature was 1.5 months, while the stable time of 5.0% hydrogel at room temperature could be up to 7 months. These indicated that the bifunctional hydrogel prepared in the present invention was very stable, which was beneficial to the storage of hydrogel at room temperature, and the stability performance of 5.0% hydrogel was the best.

Table 1 shows the gelation properties of the bifunctional hydrogels prepared in Examples 2~3 and 5~6 of the present invention. As shown in Table 1, nucleoside analogs could self-assemble to form hydrogels in both $dH_2O$ and PBS, and the gelation performance of hydrogel was mainly affected by the concentration of nucleoside analog, while the type of solvent has almost no effect on its performance. As the concentration of nucleoside analogue increased, the gelation time of the hydrogel decreased, the stabilization time was elongated, and the transition temperature (transition temperature denotes the temperature at which the hydrogel begins to transform from the gel state to the liquid state) became higher. When the concentration of nucleoside analog was more than 2.5 w/v %, the transition temperature of hydrogel was higher than 38° C. This indicated that as the concentration of nucleoside analog increased, it was easier to gel, and the resultant hydrogel would be more stable in vivo. At the same time, the bifunctional hydrogel of the present invention was completely thermoreversible.

TABLE 1

Gelation properties of the bifunctional hydrogels according to the present invention.

| Concentration of nucleoside analog (w/v %) | Solvent | Gelation time (min) | Stable time (month) | Transition temperature (° C.) | thermor-ever sibility |
|---|---|---|---|---|---|
| 2.5 | $dH_2O$ | 5 | 1.5 | 37 | Yes |
| | PBS | 4 | | | |
| 5.0 | $dH_2O$ | 1.8 | >4 | 47 | Yes |
| | PBS | 3 | | | |

According to experimental example 1, the hydrogel of the present invention had a short gelation time and good stability, and could exist stably in the body. Among them, 5.0% hydrogel had a faster gelation time and better stability, which was the best hydrogel.

Experimental Example 2 Detection of Shear-Thinning, Self-Repairing, and Injectable Performances of the Bifunctional Hydrogel According to the Present Invention 1. Experimental Method The self-repairing performance of 2.5% hydrogel and 5.0% hydrogel prepared in Examples 2~3 and Examples 5~6 was detected by cyclic strain time scanning in a rheometer; the injectability of the hydrogels of Examples 2~3 were investigated by injecting with a syringe. The conditions for cyclic strain time scanning in a rheometer were as follows: the hydrogel was added to the parallel plate preheated at 80° C., and then a thin layer of silicone oil was coated in the exposed surface of the sample around the parallel plate, to prevent water evaporation in the experimental procedures. All tests are performed at 25° C.

2. Experimental Results (1) Test Results by a Rheometer

Figure 2:
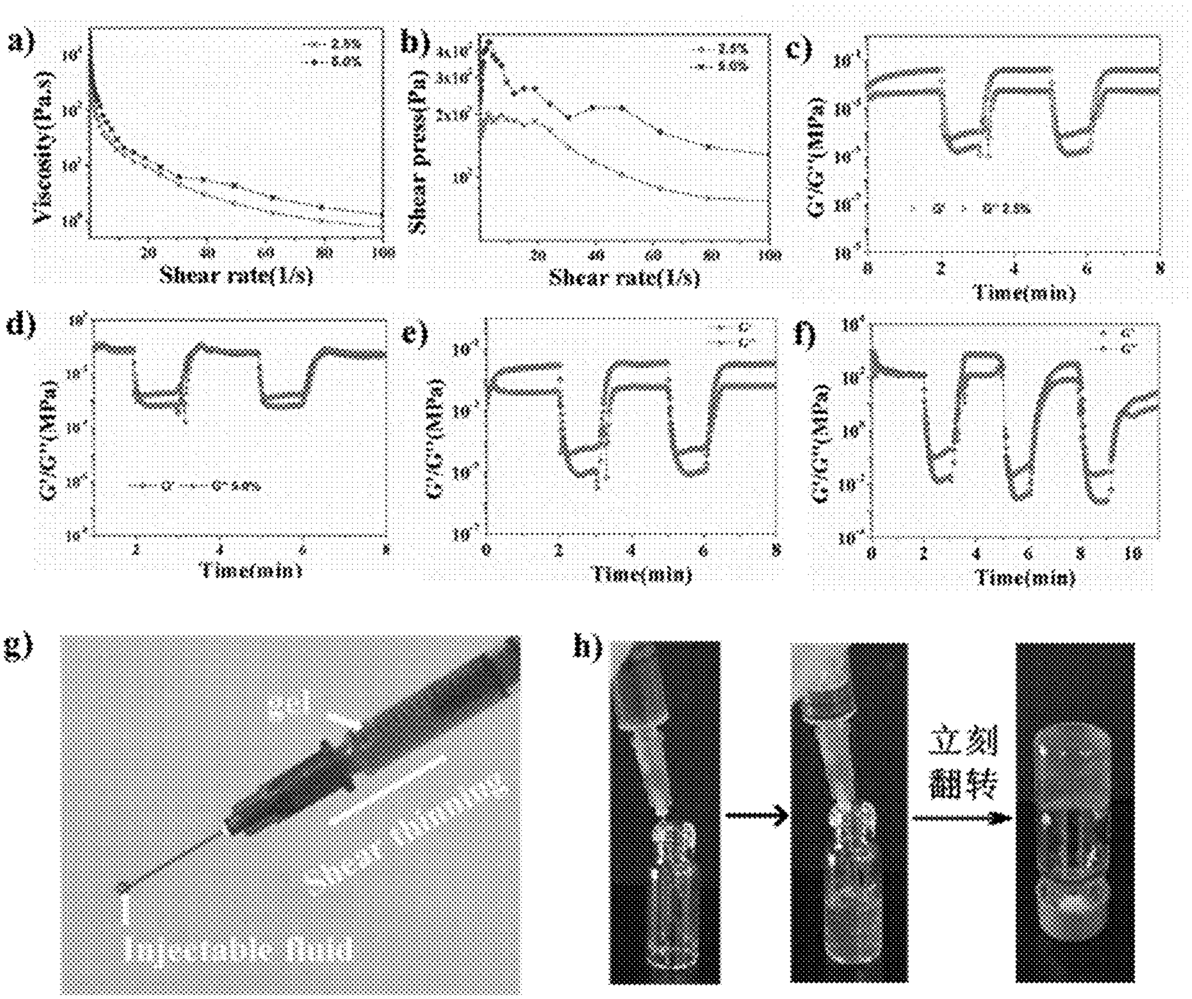
FIG. 2 shows the results of shear-thinning performance, self-repairing ability, and injectable properties of the bifunctional hydrogel according to the present invention: a)~b) The experimental results of the shear viscosity for 2.5% hydrogel of Example 2 and 5.0% hydrogel of Example 3; c)~f) are the results of scanning and evaluating the self-repairing ability of the hydrogel when the cyclic strain time $\omega$=1 rad·s$^{-1}$, in which c) 2.5% hydrogel in the solvent d$H_2O$, d) 5.0% hydrogel in the solvent d$H_2O$, e) 2.5% hydrogel in the solvent PBS, f) 5.0% hydrogel in the solvent PBS; g)~h) 2.5% hydrogel and 5.0% hydrogel were injected by syringe at room temperature (25° C.), where g) 2.5% hydrogel and h) 5.0% hydrogel.

In FIG. 2, a) and b) show the test results of shear viscosity for 2.5% hydrogel of Example 2 and 5.0% hydrogel of Example 3. As shown in a) and b) of FIG. 2, the viscosity of both 2.5% hydrogel and 5.0% hydrogel decreased as the increase of shear rate, and the shear stress dropped sharply, indicating that the hydrogel prepared in the present invention all had shear-thinning properties and could be used for injection.

Elasticity and fluid properties were measured by storage modulus and loss modulus, that were denoted as G' and G", respectively. G'<G" indicated that the test sample was in a solution state; G'>G" indicated that the test sample was in a gel state. Under stable viscoelastic conditions, the self-repairing ability of the hydrogel was evaluated by the cyclic strain time scanning at $\omega=1$ rads·s$^{-1}$, and the results are shown in c)~f) of FIG. 2. From c) to f) in FIG. 2, it could be seen that each group of hydrogels exhibited gelation properties at a strain of 1%. When the strain directly increased to 100% (in the second minute), G' and G" dropped rapidly, and G'<G" indicated that the gel was destroyed and the state of the hydrogel changed from gelation to fluid. When the strain recovered to 1%, the sample completed the fluid-gel transition within a few seconds (about 0.17 s when the solvent was PBS, while about 0.155 s when the solvent was $dH_2O$), as well as G' and G" values were completely restored to be equal to the initial modulus. It was important that after a few cycles of cyclic strain, the values of G' and G" were still equal to the initial values. It indicated that the bifunctional hydrogel of the present invention not only had injectability, but also it could change from gel to fluid when pressure was applied, having good self-repairing performance. After the pressure was removed, it could change from fluid to gel immediately.

(2) Experimental Results of Injection by Syringe

In FIG. 2, g) and h) showed the shear-thinning and injectability of the hydrogel. As shown in g) of FIG. 2, when a shear force was applied, 2.5% hydrogel was transformed to a fluid material. As shown in h) of FIG. 2, 5.0% hydrogel was injected into an empty bottle by a syringe at room temperature or 37° C., and the hydrogel would turn into a solution state when the sample was injected. The vial would be inverted immediately after injection, and then the solution would quickly return to gel state. The transition between solution and gel took only a few seconds. The experimental results of syringe injection are consistent with the results of c)~f) in FIG. 2. Once the injection shear force was removed, the hydrogel could quickly return to the gel state at the injection site.

The above experimental results indicated that the hydrogel of the present invention had good performances of shear-thinning and self-repairing. The hydrogel had good injection performance and could quickly change between solution state and gel state.

Experimental Example 3 Study on the Mechanical Performance of the Bifunctional Hydrogel of the Present Invention 1. Experimental Method 2.5% hydrogel and 5.0% hydrogel prepared in Examples 2~3 and Examples 5~6 were subjected to the mechanical performance testing. The test conditions were: Anton Paar modular intelligent rotary rheometer (MCR302) was used in the rheological test of the hydrogel. The hydrogel prepared was added to the parallel plate preheated at 80° C., and then a thin layer of silicone oil was coated in the exposed surface of the sample around the parallel plate, to prevent water evaporation in the experimental procedures. All tests are performed at 25° C., with a detection frequency range of 0.1~100 rad/s.

2. Experimental Results

Figure 3:
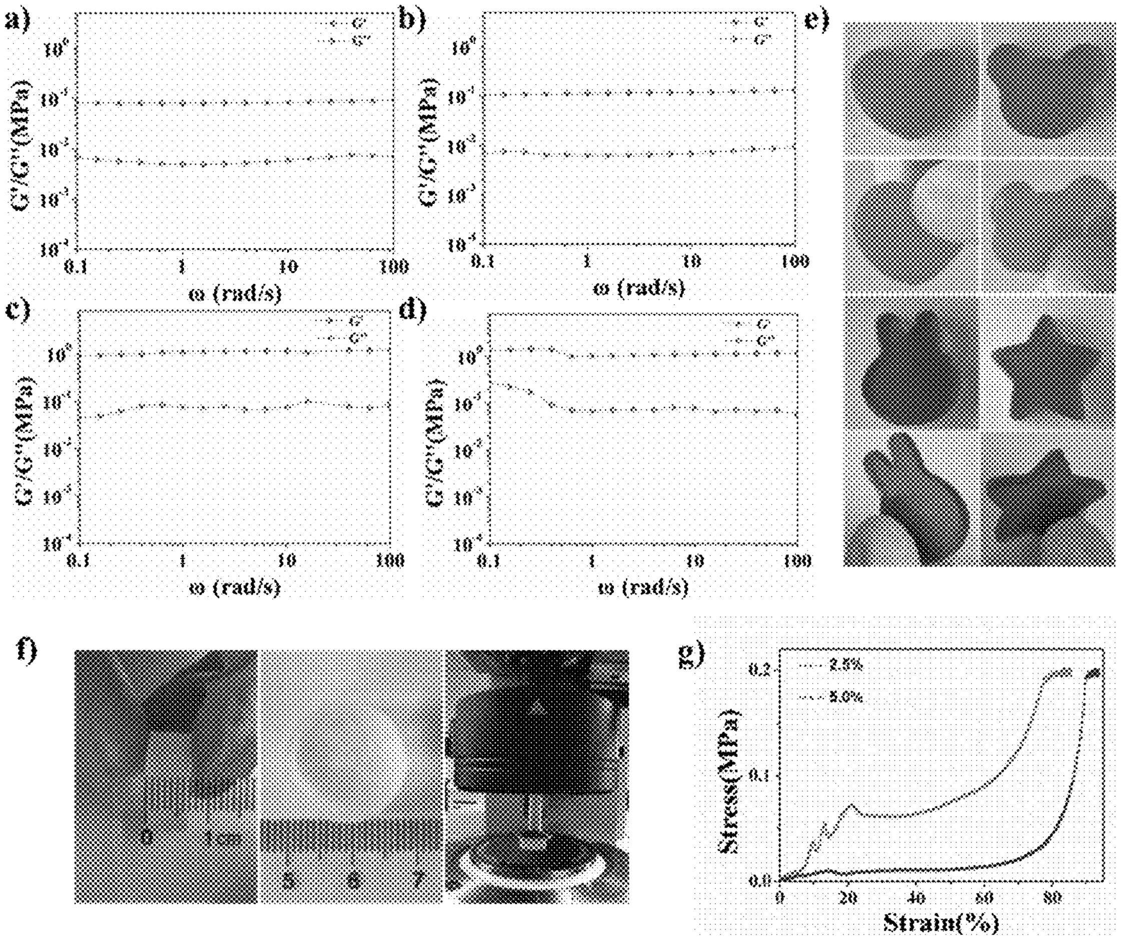
FIG. 3 shows the mechanical properties of the bifunctional hydrogel of the present invention: a)~d) The results of frequency scanning for different concentrations of hydrogels, where a) 2.5% hydrogel in the solvent d$H_2O$, b) 2.5% hydrogel in the solvent PBS, c) 5.0% hydrogel in the solvent d$H_2O$, d) 5.0% hydrogel in the solvent PBS; e) 5.0% hydrogel containing a small amount of Thioflavin T (ThT) or methylene blue, that is made into different shapes; f) The puncture diagram of the hydrogel sample; g) The mechanical test results of 2.5% hydrogel and 5.0% hydrogel.

The mechanical properties of hydrogels were further investigated by rheology testing. In the frequency range applied to the hydrogel, G' and G" hardly changed, and G' was always greater than G" (as shown in FIG. 3*a~d*), indicating that all tested samples were always in a gel state. In addition, the storage modulus of hydrogels was extremely high: the storage modulus of 2.5% hydrogel was greater than 0.1 MPa, while the storage modulus of 5.0% hydrogels was greater than 1 MPa. 5.0% hydrogel with a small amount of Thioflavin T (ThT) or methylene blue could be successfully formed into various shapes with a thickness of about 1 cm and held in the hand (as shown in FIG. 3*e*). As shown in FIG. 3*f*, all hydrogel samples could withstand a certain compressive stress without being damaged, and high-concentration hydrogels could stand higher compressive stress. As shown in FIG. 3*g*), the hydrogels of Examples 2 and 3 were tested at 25° C., the strain increased continuously in the range of 0~100%. 2.5% hydrogel could stand up more than 70% strain, with an anti-compressive strength of up to 0.2 MPa. 5.0% hydrogel could resist more than 80% strain, having an anti-compressive strength of up to 0.2 MPa.

Experimental results indicated that the hydrogel of the present invention had MPa-level storage modulus and anti-compressive strength, such as the storage modulus of 5.0% hydrogel was as high as 1 MPa, and the anti-compressive strength was as high as 0.2 MPa.

Experimental Example 4. Research on the Antibacterial Properties of the Bifunctional Hydrogel According to the Present Invention 1. Antibacterial Properties of the Bifunctional Hydrogel According to the Present Invention Against *Staphylococcus aureus* and *Escherichia coli*

1) Experimental Method

G(+) *Staphylococcus aureus* (*S. aureus*) and G(−) *Escherichia coli* (*E. coli*) were used as the representative strains of the model strains, and the antibacterial activity of 5.0% hydrogel prepared in Example 3 was initially determined by the bacterial colony counting method. The experimental procedures were as follows:

5.0 wt % hydrogel (60 μL) was directly formed in a 1.5 mL centrifugal tube according to the method described in Example 3, and then it was sterilized in an ultra-clean bench under ultraviolet light for 30 min. The same volume of PBS was added to a new 1.5 mL centrifugal tube as PBS control Group (PBS group), and 1.5 mL untreated centrifugal tube was used as the control group (n=3 for each group). The bacterial culture was diluted to $10^5$ CFU/ml with sterile LB medium, and then 100 μL bacterial solution was added to each centrifugal tube. After incubating at 37° C. for 24 h, the bacteria in each 1.5 mL centrifugal tube were respectively diluted according to the same gradient, and the same volume of the dilution was inoculated in Luria-Bertani media, then cultivated at 37° C. After incubation for 24 h, bacterial colonies were counted to determine the in vitro bactericidal activity of the hydrogel according to the present invention.

2) Experimental Results

Figure 4:
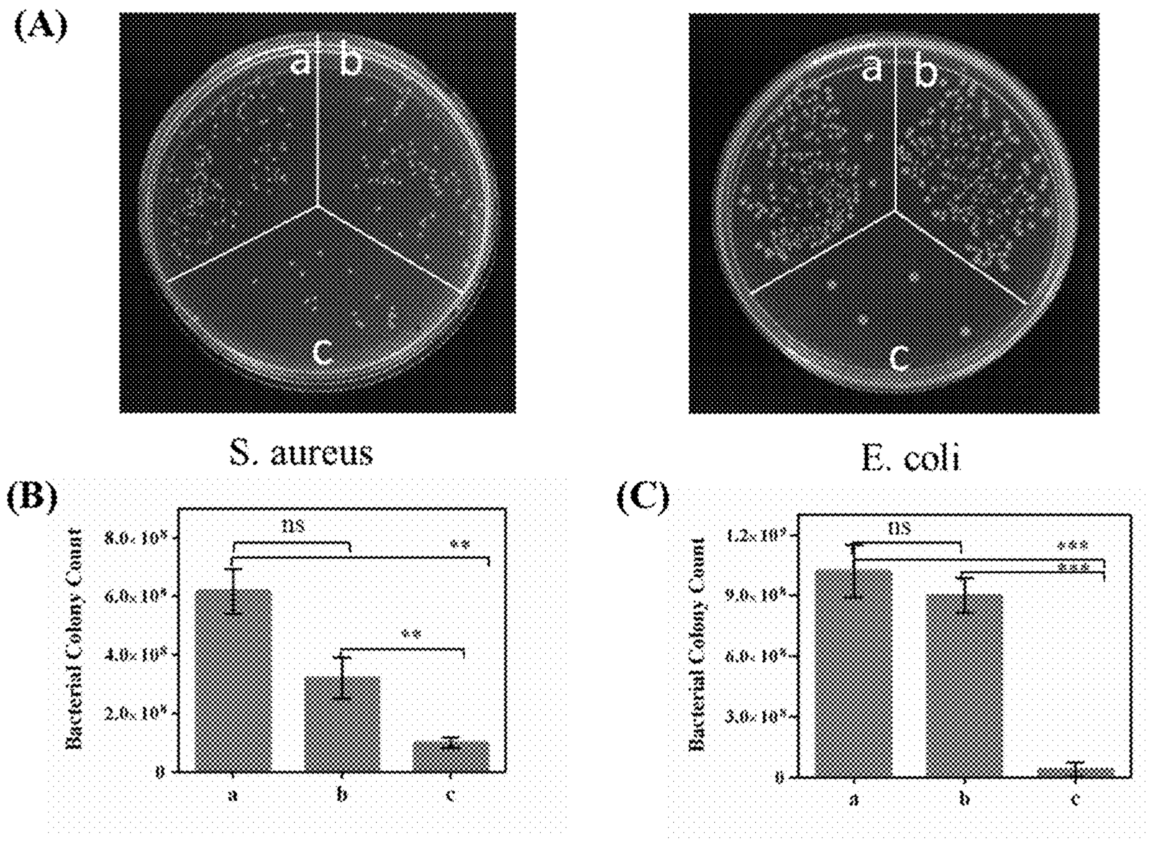
FIG. 4 shows the inhibitory effect of 5.0% hydrogel of the present invention on *Staphylococcus aureus* and *Escherichia coli*: (A) The colony morphology of *S. aureus* and *E. coli* in each group. The left picture is for *S. aureus* and the right picture is for *E. coli*; (B) The count of *S. aureus* colonies in each group; (C) The count of *E. coli* colonies in each group; in the Figure, a represents the control group, b represents the PBS group, and c represents the hydrogel group.
Figure 5:
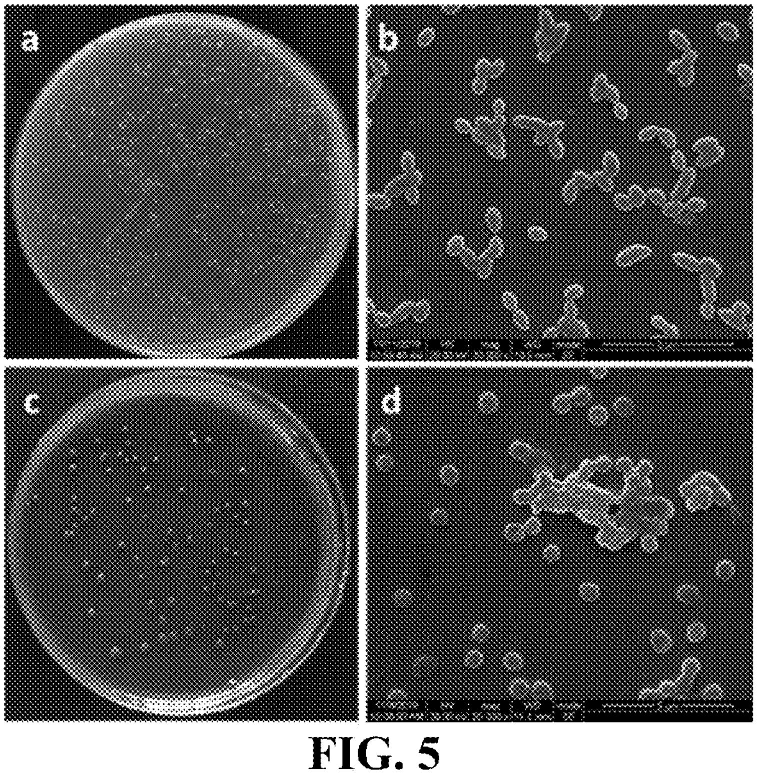
FIG. 5 shows the identification results of *Streptococcus mutans* and *Porphyromonas gingivalis*: a is the colony morphology of *Streptococcus mutans, b* is the SEM image of *Streptococcus mutans, c* is the colony morphology of *Porphyromonas gingivalis*, and d is the SEM image of *Porphyromonas gingivalis*.

16SRNA identification results confirmed that the strains were *Staphylococcus aureus* and *Escherichia coli*. The antibacterial activities of the bifunctional hydrogel according to the present invention against *S. aureus* and *E. coli* were shown in FIG. 4. As shown in FIG. 4, the result of bacterial colony counting was: the number of bacterial colonies in the control group was greater than that in PBS group, but there is no significant difference between the control group and PBS group (P>0.05), indicating that PBS didn't affect the growth of bacterial cultures, but only played a dilution effect on bacterial suspension. Compared with PBS group, 5.0% hydrogel group had fewer bacterial colonies (P<0.05), indicating that the bifunctional hydrogel of the present invention had significant antibacterial properties against both *S. aureus* and *E. coli*.

2. Antibacterial Properties of the Bifunctional Hydrogel According to the Present Invention Against the Main Pathogenic Bacteria in the Oral Cavity 1) Experimental Method G(+) *Streptococcus mutans* (*S. mutans*) and G(−) *Porphyromonas gingivalis* were used as representative strains of oral pathogens, and the antibacterial properties of the bifunctional hydrogels prepared in Examples 2 and 3 were investigated by bacterial colony counting method under scanning electron microscope. The experimental procedures were as follows: According to the methods described in Examples 2 and 3, 2.5% hydrogel (1 mL) and 5.0% hydrogel (1 mL) were prepared in a 15 mL centrifugal tube, and sterilized by ultraviolet light in an ultra-clean bench for 30 min. The same volume of PBS was added in a new 15 mL centrifugal tube as PBS control group (PBS group), and an untreated 15 mL centrifugal tube was used as control group (n=4 for each group). The bacterial culture was diluted to $10^7$ CFU/mL with sterile BHI media, and then 2 mL bacterial solution was added to each centrifugal tube, followed by culturing at 37° C. *Streptococcus mutans* was detected at the following time points: 6 h, 12 h, and 24 h. *P. gingivalis* was tested at 48 h.

100 μL bacterial solution was collected from each group at each time point mentioned above, and after performing the same gradient dilution, the same volume of the dilution was inoculated into an agar solid plate. *Streptococcus mutans* was cultured for 24 h, while *P. gingivalis* was cultured for 7 days. The in vitro bactericidal activity was determined by counting bacterial colonies. Scanning electron microscopy: the cleaned round slides were placed in a 24-well plate, and *S. mutans* bacterial solution (*Streptococcus mutans* bacterial solution) cultured for 12 hours or *P. gingivalis* bacterial solution (*Porphyromonas gingivalis* bacteria solution) cultured for 24 hours was placed on a round glass slide, fixed with an equal amount of 5% glutaraldehyde, and then subjected to gradient elution with different concentrations of ethanol (50%, 70%, 95%, 100%) for 10 min. The slide was dried naturally, and observed under the scanning electron microscope after labeling.

2) Experimental Results

Strain identification: the results from observation of colony morphology and scanning electron microscope (FIG. 5*a*~*d*) showed that the strains were *Streptococcus mutans* and *Porphyromonas gingivalis*. A single colony of *Streptococcus mutans* was milky white with the size of a small rice grain, uplifted, and rounded with neat edges. Under scanning electron microscopy, the thallus could be seen, and a single bacterial cell was spherical, or multiple bacteria connected in a chain; a single colony of *P. gingivalis* was round with neat edges, and black with metallic luster. Under the scanning electron microscope, the bacteria are oval or round with smooth edges. All are consistent with the characteristics of the standard strain.

Figure 6:
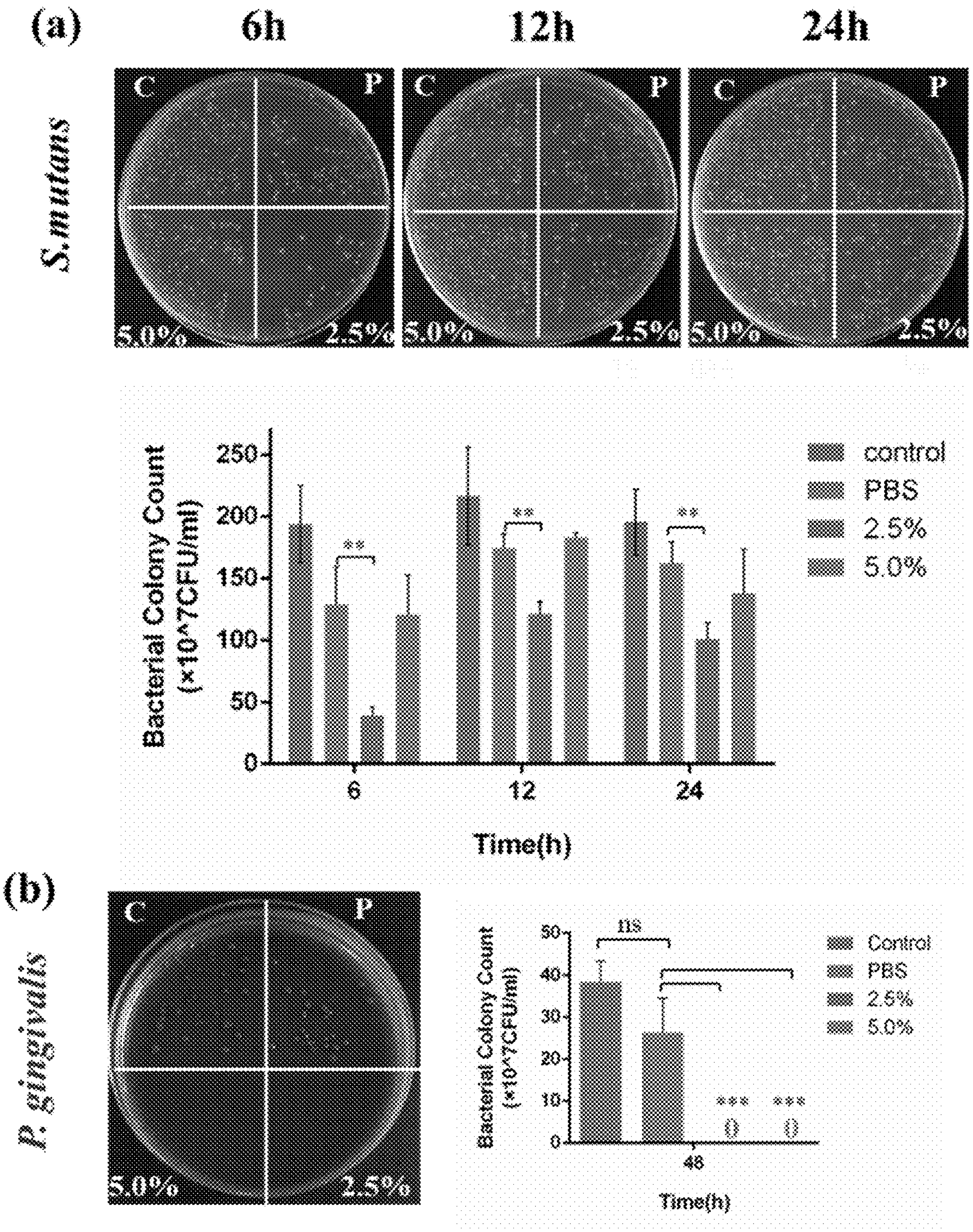
FIG. 6 shows the inhibitory effect of the bifunctional hydrogel of the present invention on *Streptococcus mutans* and *Porphyromonas gingivalis*: (a) is the inhibitory effect on *Streptococcus mutans*; (b) is the inhibitory effect on *Porphyromonas gingivalis*; In the Figure, C is the control group and P is the PBS group.

The results of bacterial colony counting were shown in FIG. 6: the control groups of *Streptococcus mutans* and *P. gingivalis* had more colonies than PBS group, but there was no significant difference (P>0.05), indicating that PBS didn't affect the growth of bacterial cultures, and only had the dilution effect on the bacterial suspension. For *Streptococcus mutans:* 2.5% hydrogel group was significantly different from PBS group (**P<0.01), indicating that 2.5% hydrogel group could effectively inhibit the growth of *Streptococcus mutans*. For *P. gingivalis*: no bacterial colony was found in both 2.5% hydrogel group and 5.0% hydrogel group, indicating that both of them could inhibit the growth of *P. gingivalis*.

Experimental results indicated that the bifunctional hydrogel of the present invention could effectively inhibit the growth of bacteria, especially the growth of the main pathogenic bacteria *Streptococcus mutans* and *P. gingivalis*. Among them, 2.5% hydrogel had a good inhibitory effect on both *Streptococcus mutans* and *P. gingivalis*, while 5.0% hydrogel had a good inhibitory effect on *P. gingivalis*.

Experimental Example 5. Evaluation of the Biocompatibility of the Bifunctional Hydrogel According to the Present Invention 1. In Vitro Cytotoxicity Evaluation of the Bifunctional Hydrogel According to the Present Invention 1) Experimental Method The cytotoxicity of the bifunctional hydrogel prepared in Examples 1 and 2 was tested in vitro. The cytotoxicity against NOK-SI cell lines were detected by CCK8 cytotoxicity test. The experimental procedures were as follows:

Well-growing NOK-SI cells were collected and prepared as cell suspensions. Their cell densities were adjusted and then inoculated in 24-well plates. After 4-6 h, the cells adhered to the wall. 5 μL hydrogels prepared in Examples 1 and 2 (experimental groups) as well as 5 μL PBS (as PBS experimental group) were respectively added in the upper of the transwell chamber, and then placed in a 24-well plate, and co-cultured at 37° C. for 24 h. Then, 10% CCK8 reagent was added, and incubated for 3 h. The blank well was used to adjust the zero point, and a microplate reader was used to detect the absorbance (OD) at the wavelength of 450 nm. Multiple wells (≥3) was set up for each group, and the results were averaged. Each experiment was independently repeated 3 times. A cell control group (control group, Control) was included in the experiment. Percentage of cell viability (%)=experimental group (OD)/control group (OD)×100%.

2) Experimental Results

Figure 7:
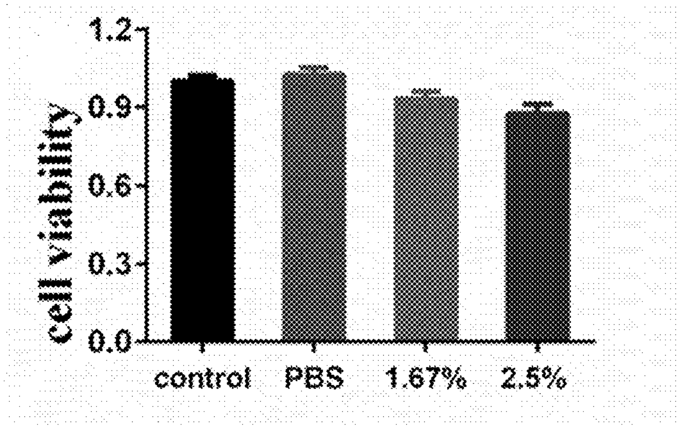
FIG. 7 shows the toxicity of the hydrogel of the present invention to NOK-SI cell lines.

The cytotoxicity of the hydrogel according to the present invention against NOK-SI cell lines was evaluated by CCK8 kit. The result was shown in FIG. 7 (the viable cell data in FIG. 7 were not multiplied by 100%, and was the direct results of experimental group (OD)/control group (OD)). The results in FIG. 7 showed: The cell viability in 1.67% hydrogel and 2.5% hydrogel was as high as 95% and 90%, respectively, indicating that the hydrogel material of the present invention was non-toxic or low-toxic to cells and had good cell compatibility. The hydrogel of the present invention had no acute toxicity in vitro, with potential applications as biological materials.

2. In Vivo Toxicity Evaluation of the Bifunctional Hydrogel According to the Present Invention 1) Experimental Method After subcutaneous injection of the bifunctional hydrogel prepared in Examples 1 and 2 in the back of female BALB/c mice, the degradation was detected. And at a certain time points (0 h, 3 h, 6 h, 9 h, 12 h, 15 h, 18 h, 21 h and 24 h), the blood was collected and divided into 2 parts, and the blood was subjected to complete blood count and serum biochemical test for biocompatibility. The mice were sacrificed and the heart, liver, spleen, lung, and kidney were processed for HE staining. The organs were observed for damage. An equal amount of PBS was injected into the back of BALB/c mice as PBS group and used as the control.

2) Experimental Results

Figure 8:
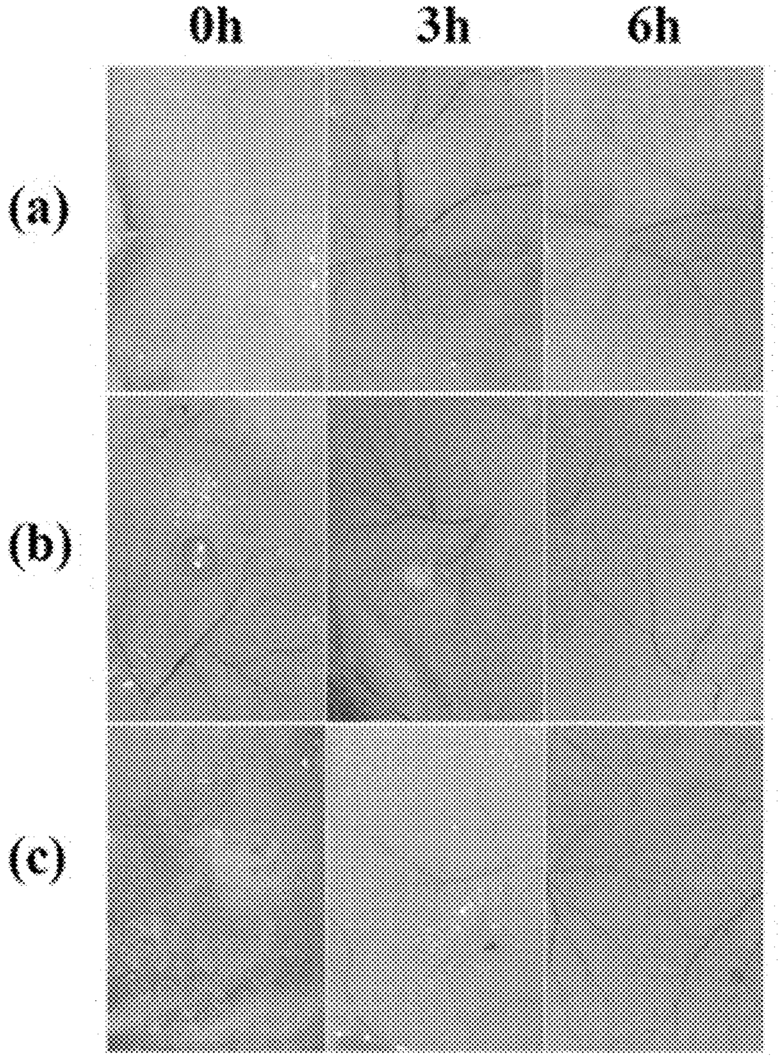
FIG. 8 shows the degradation of the hydrogel of the present invention at 0 h, 3 h and 6 h in mice. In the Figure, (a) PBS group, (b) 1.67% hydrogel group, and (c) 2.5% hydrogel group.
Figure 9:
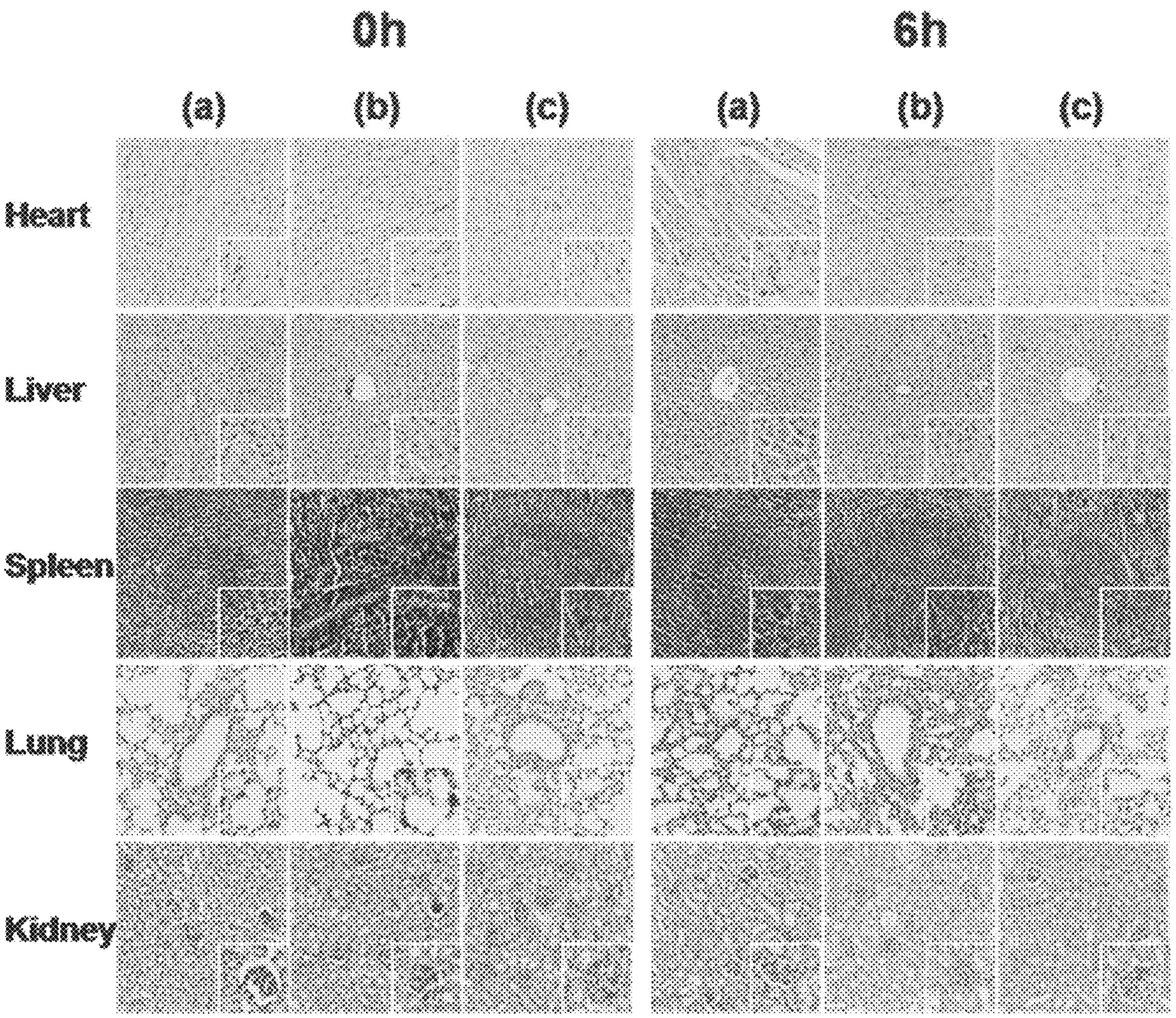
FIG. 9 shows HE staining of heart, liver, spleen, lung, and kidney after the hydrogel of the present invention is injected into mice. In the Figure, (a) PBS group, (b) 1.67% hydrogel group, (C) 2.5% hydrogel group.

The degradation of the material and its biological safety were detected by submucosal injection of hydrogel in the back of mice. The evaluation indexes included complete blood count (CBC), serum biochemical indicators and histology. FIG. 8 showed the degradation of the hydrogel according to the present invention in mice. The results of FIG. 8 indicated that the hydrogel degraded within 6 hours, and the degradation rate of 1.67% hydrogel was faster than that of 2.5% hydrogel. FIG. 9 showed the results of hematoxylin and eosin (H&E) staining. The staining results showed that the heart, liver, spleen, lung and kidney of 1.67% hydrogel and 2.5% hydrogel treatment groups were all compared with the control group, and no obvious signs of organ damage were found.

Figure 10:
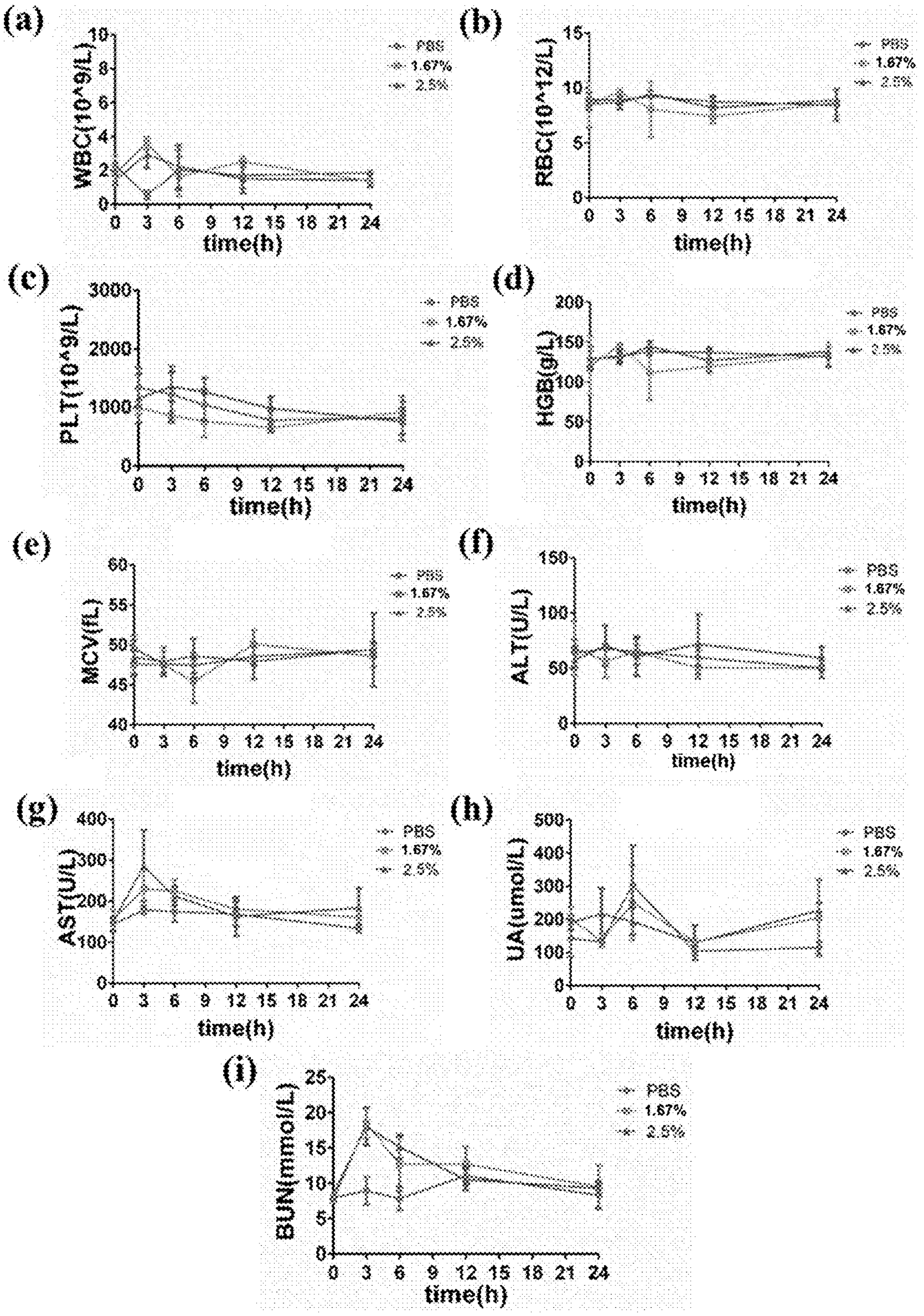
FIG. 10 shows the complete blood count and the biocompatibility results by serum biochemical test: (a) The white blood cell (WBC) count; (b) The red blood cell (RBC) count; (c) The platelet (PLT) count; (d) The hemoglobin (HGB) concentration; (e) The mean corpuscular volume (MCV); (f) The content of alanine transaminase (ALT, liver function index); (g) The content of aspartate transaminase (AST, liver function index); (h) The content of uric acid (UA, renal function index), (i) The content of urea nitrogen (BUN, renal function index).

In addition, as shown in FIG. 10, compared with PBS group, each CBC indicator of the treatment group was not different (P>0.05), except for white blood cells (WBC) 3 h after injection of the hydrogel. For WBC at the third hour after hydrogel injection, 1.67% hydrogel group (p=0.00, ***P<0.001) and 2.5% hydrogel group (P=0.03, *P<0.05) were higher than those of PBS group, but their values are within the normal range. This difference might be due to individual differences between animals. For serum biochemical indicators, compared with PBS treatment group, 1.67% hydrogel group showed a decrease in blood urea nitrogen (BUN, *P<0.05) and an increase in aspartate transaminase (AST, *P<0.05) 3 hours after injection, but there was no significant difference in other serum biochemical indicators (P>0.05). In 2.5% hydrogel group, except for the decrease of plasma BUN (*P<0.05) 3 hours after injection and the increase of uric acid (UA,*P<0.05) 24 hours after injection, there was no difference in other test indicators. However, all the detected values are within the normal range. The test results showed that the bifunctional hydrogel of the present invention had no acute toxicity in vivo.

The above experimental results showed that the bifunctional hydrogel of the present invention had good degradation performance and biocompatibility both in vivo and in vitro.

In summary, a bifunctional hydrogel was prepared in the present invention by a simple and green method. The hydrogel had good shear-thinning and self-repairing performances, good injectability, quick gelling, and was easy to use. The hydrogel also had excellent mechanical properties, as well as extremely high strength, storage modulus and anti-compressive strength up to MPa level. At the same time, the hydrogel had a good antibacterial effect, and had a good inhibitory effect on the growth of model strains and oral pathogens. In addition, the hydrogel had good stability at room temperature, could be stored for a long time, and could be quickly degraded after being implanted in the human body, and had good biocompatibility. With these outstanding features, the hydrogel of the present invention was expected to be a candidate drug for the local injection treatment of periodontal disease, and it also had potential application prospects in the minimally invasive treatment of craniofacial bone tissue defects

The invention claimed is:

1. A hydrogel, comprising a 3-D network consisting of nucleoside analog of Formula I and a solvent, wherein a concentration of the nucleoside analog in the hydrogel is 2.5 w/v % to 5 w/v %, Formula I

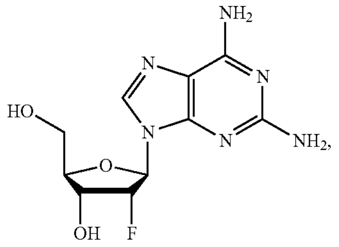

wherein the solvent is water or phosphate-buffered saline.

2. A preparative method of the hydrogel according to claim 1, comprising:

dissolving the nucleoside analog in the solvent under heating to form a solution, and then cooling the solution to room temperature.

3. A drug composition, comprising the hydrogel of claim 1 and one or more pharmaceutically acceptable excipient or auxiliary.

4. A method for repairing a cranio-maxillofacial bone tissue, comprising applying the drug composition of claim 3 to a subject in need thereof.

5. A method for treating a periodontal disease, comprising applying a drug composition of claim 3 to a subject in need thereof.

6. The method according to claim 5, wherein the periodontal disease is periodontitis.

7. The method according to claim 5, wherein the drug composition is applied by local injection to a periodontal pocket.

8. The hydrogel according to claim 1, wherein a concentration of the nucleoside analog in the hydrogel is 2.5 w/v %.

* * * * *